(12) United States Patent
Thalgott et al.

(10) Patent No.: US 9,233,010 B2
(45) Date of Patent: Jan. 12, 2016

(54) SPINAL IMPLANT CONFIGURED FOR LATERAL INSERTION

(71) Applicant: CENTINEL SPINE, INC.

(72) Inventors: John S. Thalgott, Las Vegas, NV (US); David T. Stinson, Woodinville, WA (US); John J. Viscogliosi, New York, NY (US)

(73) Assignee: CENTINEL SPINE, INC., New York, NY (US)

( * ) Notice: Subject to any disclaimer, the term of this patent is extended or adjusted under 35 U.S.C. 154(b) by 0 days.

(21) Appl. No.: 14/551,858

(22) Filed: Nov. 24, 2014

(65) Prior Publication Data

US 2015/0081027 A1    Mar. 19, 2015

Related U.S. Application Data

(62) Division of application No. 12/941,193, filed on Nov. 8, 2010, now Pat. No. 8,894,708.

(60) Provisional application No. 61/259,401, filed on Nov. 9, 2009.

(51) Int. Cl.
*A61F 2/44* (2006.01)
*A61B 17/86* (2006.01)
(Continued)

(52) U.S. Cl.
CPC ............... *A61F 2/447* (2013.01); *A61F 2/4455* (2013.01); *A61B 17/86* (2013.01); *A61F 2002/2817* (2013.01); *A61F 2002/3008* (2013.01); *A61F 2002/30062* (2013.01);
(Continued)

(58) Field of Classification Search
CPC ......... A61F 2/44; A61F 2/4455; A61F 2/447; A61F 2002/4475; A61F 2002/30787; A61F 2002/30604; A61F 2002/30794; A61F 2002/30578; A61F 2002/30782
USPC ............................................ 623/17.11–17.16
See application file for complete search history.

(56) References Cited

U.S. PATENT DOCUMENTS

| 4,904,261 A | 2/1990 | Dove et al. |
| 5,192,327 A | 3/1993 | Brantigan |

(Continued)

FOREIGN PATENT DOCUMENTS

WO      03053290 A1     7/2003

OTHER PUBLICATIONS

Extended European Search Report dated Nov. 20, 2013 from European Application No. 10829223.6.
(Continued)

*Primary Examiner* — Mary Hoffman
(74) *Attorney, Agent, or Firm* — MH2 Technology Law Group, LLP

(57) ABSTRACT

The embodiments provide a spinal implant that is configured for lateral insertion into a patient's intervertebral disc space. The spinal implant may have a body having a tapered anterior portion and one or more apertures. The tapered anterior portion allows for concomitant distraction of soft tissue during insertion of the implant. In addition, at least some of the apertures are designed to permit a predetermined amount of nutation by a fixation element. The fixations elements that allow nutation enable the fixation element to toggle from one position to another, for example, during subsidence of the implant in situ.

6 Claims, 7 Drawing Sheets

(51) Int. Cl.
*A61F 2/28* (2006.01)
*A61F 2/30* (2006.01)
*A61F 2/46* (2006.01)

(52) U.S. Cl.
CPC ......... *A61F 2002/30324* (2013.01); *A61F 2002/30617* (2013.01); *A61F 2002/30787* (2013.01); *A61F 2002/30794* (2013.01); *A61F 2002/30841* (2013.01); *A61F 2002/30904* (2013.01); *A61F 2002/4475* (2013.01); *A61F 2002/4629* (2013.01); *A61F 2210/0004* (2013.01); *A61F 2250/0098* (2013.01); *A61F 2310/00017* (2013.01); *A61F 2310/00023* (2013.01)

(56) References Cited

U.S. PATENT DOCUMENTS

| | | | |
|---|---|---|---|
| 5,306,307 A | 4/1994 | Senter et al. | |
| 5,425,772 A | 6/1995 | Brantigan | |
| 5,766,251 A | 6/1998 | Koshino | |
| 6,099,531 A | 8/2000 | Bonutti | |
| 6,231,610 B1 | 5/2001 | Geisler | |
| 6,241,771 B1 | 6/2001 | Gresser et al. | |
| 6,342,074 B1 | 1/2002 | Simpson | |
| 6,558,423 B1 | 5/2003 | Michelson | |
| 6,629,998 B1 | 10/2003 | Lin | |
| 6,942,697 B2 | 9/2005 | Lange et al. | |
| 6,972,019 B2 * | 12/2005 | Michelson | 606/86 A |
| 6,984,234 B2 | 1/2006 | Bray | |
| 7,077,864 B2 * | 7/2006 | Byrd et al. | 623/17.11 |
| 7,232,464 B2 | 6/2007 | Mathieu et al. | |
| 7,326,248 B2 | 2/2008 | Michelson | |
| 7,749,269 B2 | 7/2010 | Peterman et al. | |
| 7,763,078 B2 | 7/2010 | Peterman et al. | |
| 7,776,095 B2 | 8/2010 | Peterman et al. | |
| 7,846,207 B2 | 12/2010 | Lechmann et al. | |
| 7,985,255 B2 * | 7/2011 | Bray et al. | 623/17.11 |
| 7,988,734 B2 | 8/2011 | Peterman et al. | |
| 8,100,976 B2 * | 1/2012 | Bray et al. | 623/17.16 |
| 8,137,405 B2 | 3/2012 | Kostuik et al. | |
| 8,268,000 B2 * | 9/2012 | Waugh et al. | 623/17.16 |
| 8,287,597 B1 | 10/2012 | Pimenta et al. | |
| 8,377,139 B2 * | 2/2013 | Laubert et al. | 623/17.16 |
| 8,425,607 B2 | 4/2013 | Waugh et al. | |
| 8,480,747 B2 * | 7/2013 | Melkent et al. | 623/17.16 |
| 8,613,772 B2 * | 12/2013 | Bray et al. | 623/17.16 |
| 8,623,088 B1 | 1/2014 | Tohmeh et al. | |
| 8,894,708 B2 | 11/2014 | Thalgott et al. | |
| 2003/0100950 A1 * | 5/2003 | Moret | 623/17.16 |
| 2003/0130737 A1 | 7/2003 | McGahan et al. | |
| 2003/0199881 A1 | 10/2003 | Bonutti | |
| 2007/0233253 A1 * | 10/2007 | Bray et al. | 623/17.11 |
| 2008/0065219 A1 | 3/2008 | Dye | |
| 2008/0077247 A1 | 3/2008 | Murillo et al. | |
| 2008/0154375 A1 | 6/2008 | Serhan et al. | |
| 2008/0249575 A1 * | 10/2008 | Waugh et al. | 606/305 |
| 2008/0249625 A1 | 10/2008 | Waugh et al. | |
| 2009/0030520 A1 * | 1/2009 | Biedermann et al. | 623/17.16 |
| 2009/0210062 A1 * | 8/2009 | Thalgott et al. | 623/17.16 |
| 2010/0152853 A1 | 6/2010 | Kirschman | |
| 2012/0078373 A1 * | 3/2012 | Gamache et al. | 623/17.16 |

OTHER PUBLICATIONS

International Search Report dated Jan. 4, 2011 from International Application No. PCT/US2010/055811, pp. 1-3.

Patent Examination Report No. 1 dated Mar. 3, 2015 from Australian Application No. 2010314954, pp. 1-3.

* cited by examiner

1

SPINAL IMPLANT CONFIGURED FOR LATERAL INSERTION

CROSS-REFERENCE TO RELATED APPLICATIONS

This application is a divisional of U.S. patent application Ser. No. 12/941,193, filed Nov. 8, 2010 (allowed), which claims benefit of U.S. Provisional Application No. 61/259,401, filed Nov. 9, 2009, and entitled "SPINAL IMPLANT CONFIGURED FOR LATERAL INSERTION," the entire contents of which are incorporated herein by reference.

FIELD

The present disclosure relates to orthopedic implants, and more particularly to spinal implants that facilitate fusion of bone segments and associated methods. Even more particularly, the present disclosure relates to a spinal fusion implant configured for lateral insertion.

BACKGROUND

The integrity of the spine, including its subcomponents like the vertebral bodies and intervertebral discs that are well known structural body parts forming the spine, is key to a patient's health. These parts may become crushed or damaged as a result of trauma or injury, or damaged by disease (e.g., by tumor, autoimmune disease), or as a result of wear over time or degeneration caused by the normal aging process.

In many instances, one or more damaged structural body parts can be repaired or replaced with a prosthesis or implant. For example, specific to the spine, one method of repair is to remove the damaged vertebra (in whole or in part) and/or the damaged disc (in whole or in part) and replace it with an implant or prosthesis. In some cases, it is necessary to stabilize a weakened or damaged spinal region by reducing or inhibiting mobility in the area to avoid further progression of the damage and/or to reduce or alleviate pain caused by the damage or injury. In other cases, it is desirable to join together the damaged vertebrae and/or induce healing of the vertebrae. Accordingly, an implant or prosthesis may be configured to facilitate fusion between two adjacent vertebrae. The implant or prosthesis may be placed without attachment means or fastened in position between adjacent structural body parts (e.g., adjacent vertebral bodies).

Typically, an implant or prosthesis is secured directly to a bone structure by mechanical or biological means. One manner of spine repair involves attaching a fusion implant or prosthesis to adjacent vertebral bodies using a fixation element, such as a screw. Most implants and their attachment means are configured to provide an immediate, rigid fixation of the implant to the implantation site. Unfortunately, after implantation the implants tend to subside, or settle, into the surrounding environment as the patient's weight is exerted upon the implant. In some cases, this subsidence may cause the rigidly fixed attachment means to either loosen, dislodge or potentially damage one or more of the vertebral bodies.

Several known surgical techniques can be used to implant a spinal prosthesis. The suitability of any particular technique may depend upon the amount of access available to the implant site. For instance, a surgeon may elect a particular entry pathway depending on the size of the patient or the condition of the patient's spine such as where a tumor, scar tissue, or other obstacle is present. Other times, it may be desirable to minimize intrusion into the patient's musculature and associated ligamentous tissue. In some patients who have had prior surgeries, implants or fixation elements may have already been inserted into the patient's spine and as such, an implant introduction pathway may have to account for these prior existing conditions.

Thus, it is desirable to provide an implant that can be easily inserted in accordance with a specific pathway or approach. For example, in certain situations, it is desirable to provide a spinal implant that can be inserted using a lateral approach. It is further desirable to provide an implant that is configured to reduce insertion forces. In addition, it is desirable to provide an implant and associated fixation elements that can account for subsidence that occurs with the implant subsequent to implantation while also providing rigid fixation.

Although the following discussion focuses on spinal implants or prostheses, it will be appreciated that many of the principles may equally be applied to other structural body parts within a human or animal body.

SUMMARY

The present disclosure describes a spinal implant that is configured for lateral insertion into a patient's intervertebral disc space. In accordance with one exemplary embodiment, a spinal implant is provided having an upper surface, a lower surface, an anterior portion, a posterior portion and one or more apertures within the posterior portion for receiving at least one fixation element wherein the implant is configured for lateral insertion. For example, the anterior portion or leading edge of the implant may include a sharp, bullet shaped nose or tip. All or some of the apertures may be configured to permit a predetermined amount of nutation by a fixation element, thus allowing the fixation element to toggle from one position to another. The spinal implant may additionally include anti-migration features.

In one embodiment, a spinal implant comprises a body and one or more apertures. The body may comprise an upper surface, a lower surface, a tapered anterior portion, and a posterior portion, wherein the body is configured for lateral insertion between vertebral bodies of a patient's spine. The one or more apertures may be provided within the posterior portion of the body and can receive at least one fixation element. At least one of the apertures is configured to permit a predetermined amount of nutation by a fixation element.

In another embodiment, a method of treating a patient's spine comprises accessing at least a portion of a patient's spine via a lateral approach. A spinal implant is then inserted between vertebral bodies of the patient's spine, wherein the spinal implant comprises a body having an upper surface, a lower surface, a tapered anterior portion, a posterior portion, wherein the body is configured for lateral insertion between vertebral bodies of a patient's spine, the implant further including one or more apertures within the posterior portion of the body for receiving at least one fixation element, and wherein at least one of the apertures is configured to permit a predetermined amount of nutation by a fixation element. The spinal implant is attached with the at least one fixation elements to the vertebral bodies and a predetermined amount of toggling of the fixation element is permitted based on nutation of the fixation element during subsidence of the spinal implant.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Figure 1:
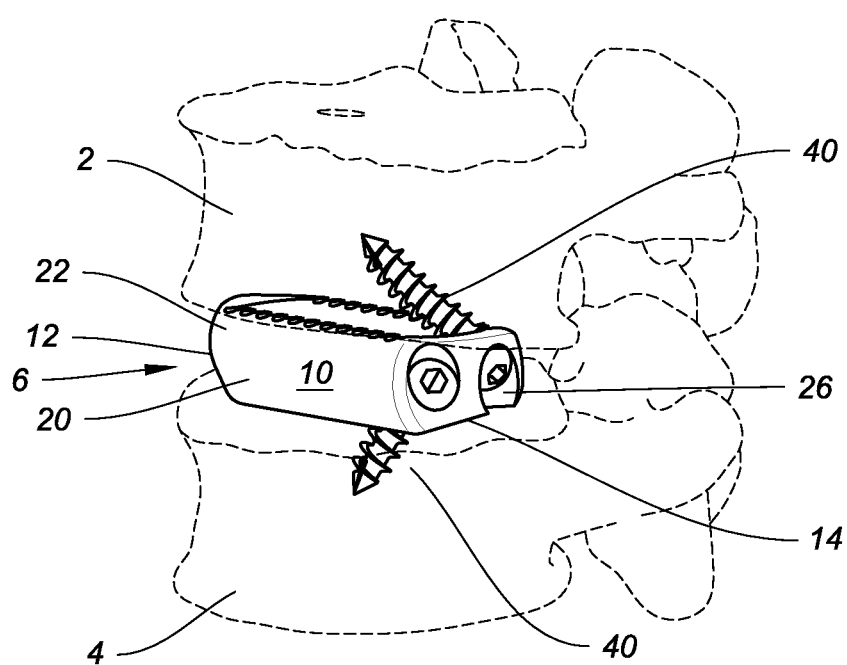
FIG. 1 illustrates a partial cutaway view of a spinal implant of the present disclosure in situ.

Referring now to FIG. 1, a spinal implant 10 of the present disclosure is shown. The spinal implant 10 may be implanted in the intervertebral space 6 between vertebral bodies 2, 4 and secured to the vertebral bodies 2, 4 with fixation screws 40. The spinal implant 10 may be employed in the lumbar or thoracic regions. Alternatively, the spinal implant 10 may be employed in the cervical region of the spine, in a manner similar to the one described for the cervical implant of U.S. patent application Ser. No. 11/938,476 filed Nov. 12, 2007, entitled "Orthopaedic Implants and Prostheses," which is herein incorporated by reference in its entirety. A cervical version may be provided so long as it is appropriately sized and configured, and the surgical approach takes into account this specific design.

As shown in FIGS. 2A-2D, the spinal implant 10 may include anterior and posterior portions 12, 14 and upper and lower surfaces 16, 18 profiled to correspond with the profile of any bone material to which they are to be secured. A pair of sidewalls 20 extends between the upper and lower surfaces 16, 18 and connects to the anterior and posterior portions 12, 14. The spinal implant 10 may include a central opening or lumen 24 extending between the upper and lower surfaces 16, 18 to facilitate bony ingrowth or fusion between adjacent bone segments, such as vertebral bodies 2, 4. If so desired, the opening 24 may be used to receive and hold bone graft material.

To facilitate ease of insertion, the anterior portion, or leading end 12 may be tapered or otherwise shaped for concomitant distraction of soft tissue during insertion. For example, the anterior portion 12 may be a sharp, bullet shaped nose or tip 22. The unique geometry of the implant 10 including this sharpened tip 22 supports reduced insertion forces, and may also help to separate tissue during the insertion. This can be helpful, for example, where scar tissue or other obstructions are present at the implantation site, or where there is stenosis and/or some other anatomic anomaly such as where the endplates have grown together.

Figure 7:
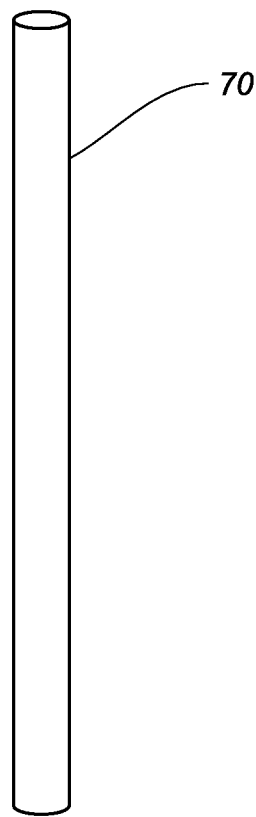
FIG. 7 illustrates an exemplary embodiment of an imaging marker of the present disclosure.

The posterior portion, or trailing end 14 of the spinal implant 10 includes holes 26 for receiving fixation elements, such as bone screws 40. In the embodiment shown, the spinal implant 10 includes two screw holes 26, one extending superiorly and one extending inferiorly (see in particular FIG. 2D). However, one skilled in the art will appreciate that the implant 10 may comprise any number of holes in any location on the implant 10. For example, instead of having one superior hole and one inferior hole in the implant 10 as shown in the drawings, the implant may have two superior holes, or may be adapted to have two inferior holes. As previously discussed, the implant 10 may be configured with any number of holes without departing from the spirit of the disclosure. In addition, the implant 10 may include bores 50 for receiving features like a radiologic marker or other imaging marker 70, as shown in FIG. 7. The imaging marker 70 may be rod-shaped, for example, for insertion into the bores 50.

The holes 26 provide a path through which securing means (e.g., fixation elements such as bone screws 40) may be inserted so as to secure the implant 10 to respective superior and inferior vertebral bodies 2, 4. The holes 26 may be configured to accommodate a variety of securing means, such as screws, pins, staples, or any other suitable fastening device. In one embodiment, the fixation screws 40 may be self-tapping and/or self-drilling and may be of a bone-screw-type, such as those well known to skilled artisans. In some embodiments, the head portion 42 of the fixation screws 40 extends into an elongate body 44 that terminates at a tip 46. While the implant 10 is shown with screws 40 sized and shaped for unicortical bone fixation, it is contemplated that bone screws sized and shaped for bicortical bone fixation may also be employed with the present disclosure.

Figure 5:
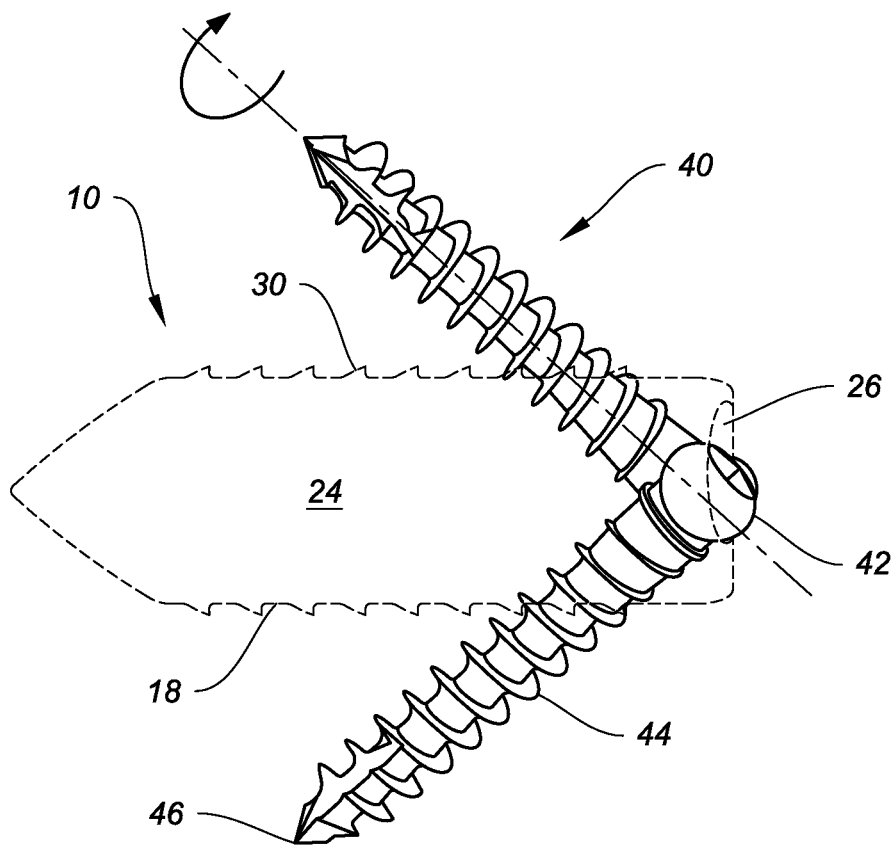
FIG. 5 illustrates a cross-sectional view of the spinal implant with fixation screws of FIG. 4.

The holes 26 of the spinal implant 10 may be configured to permit a predetermined amount of screw toggle (i.e., angular skew) and enable a lag effect when the fixation screw 40 is inserted and resides inside the hole or lumen 26. In other words, the holes 26 permit a certain degree of nutation by the screw 40 and thus the screws 40 may toggle from one position to one or more different positions, for instance, during subsidence. As depicted in FIG. 5, the holes 26 may be configured with a conical range of motion (i.e., angular clearance) of about 25 to about 35 degrees, although it is contemplated that an even larger range may be possible such as 20 to 40 degrees, or 15 to 45 degrees. In one embodiment, the range is about 22 to 28 degrees. It is also believed that the predetermined screw toggle (permitted by the clearance between the lumen, or hole 26 and the screw 40) promotes locking of the screw 40 to the implant 10 after subsidence subsequent to implantation. Alternatively, the holes 26 of implant 10 may be configured with little or no clearance to achieve rigid fixation, for example, when implant 10 is to be implanted into sclerotic bone.

Figure 2A:
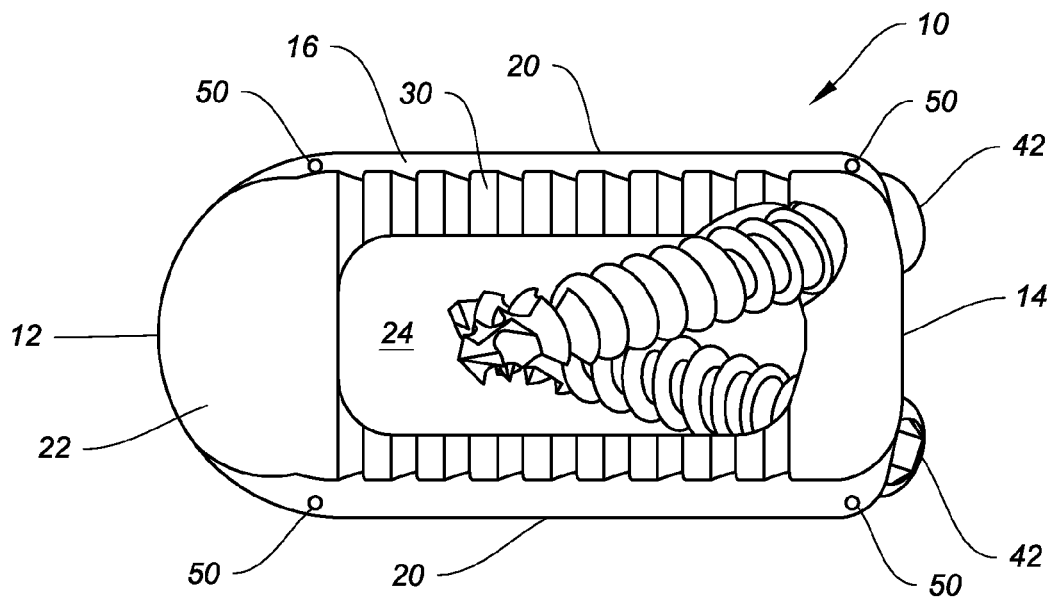
FIG. 2A illustrates a superior view of the spinal implant of FIG. 1 with fixation screws.
Figure 2B:
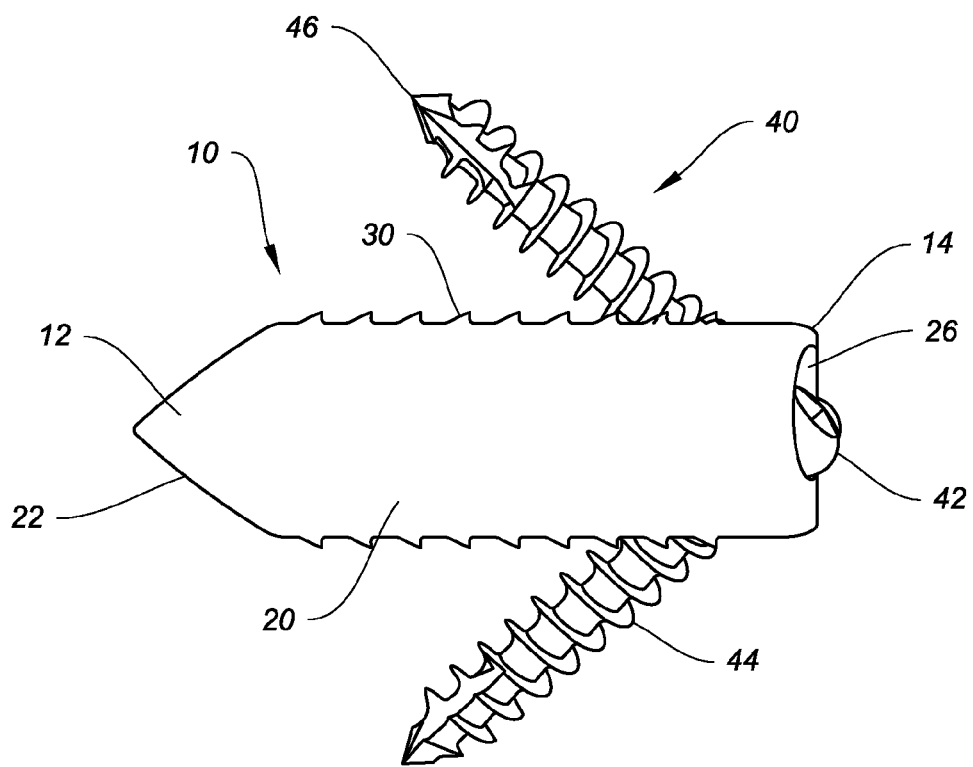
FIG. 2B illustrates a sagittal view of the spinal implant of FIG. 1 with fixation screws.
Figure 2C:
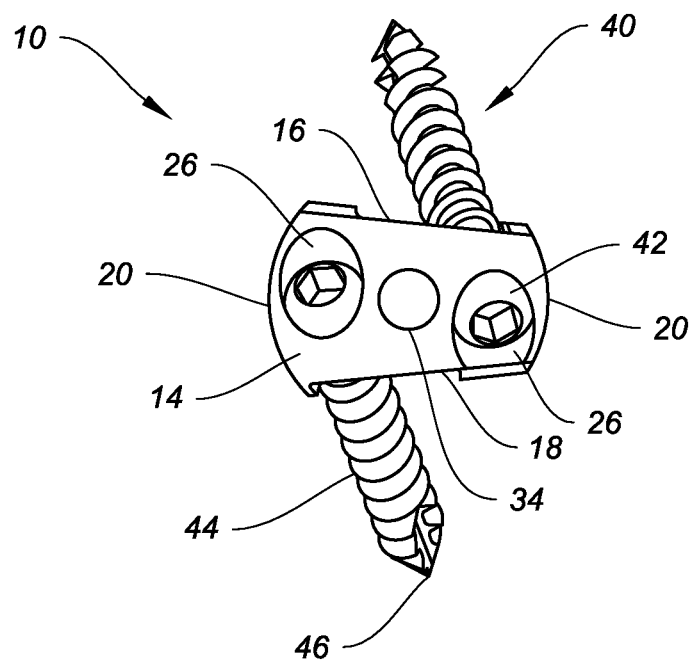
FIG. 2C illustrates a posterior view of the spinal implant of FIG. 1 with fixation screws.
Figure 2D:
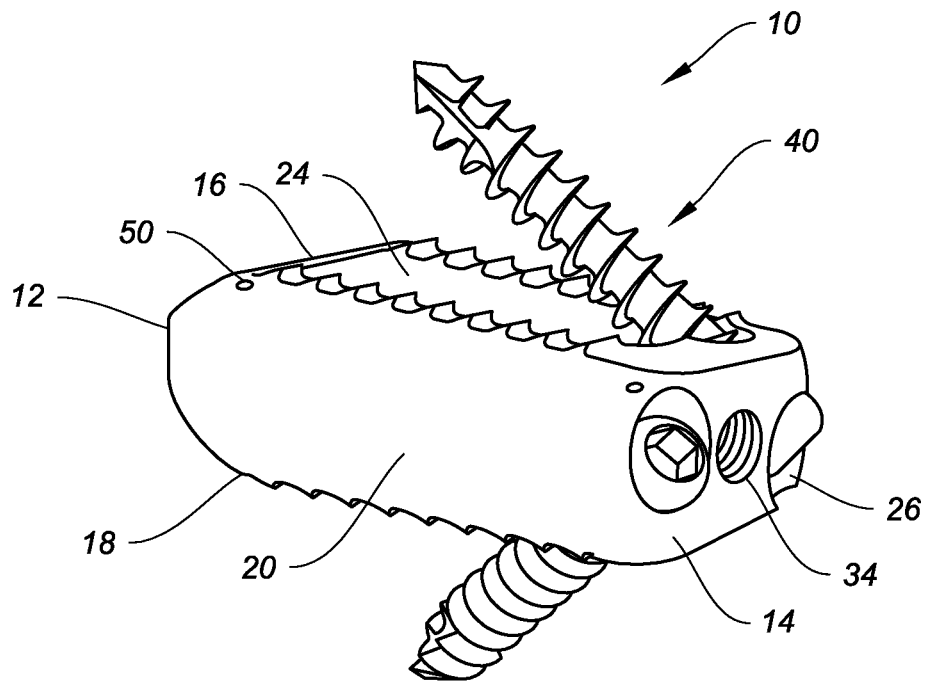
FIG. 2D illustrates a perspective view of the spinal implant of FIG. 1 with fixation screws.

As shown in FIG. 2C, the spinal implant 10 may have non-parallel upper and lower surfaces 16, 18 to form a wedge-shaped implant 10. However, one skilled in the art will appreciate that the spinal implant 10 may also be provided with parallel upper and lower surfaces 16, 18. The spinal implant 10 may have any suitable shape or size to allow it to be used under lodortic or kyphotic conditions. For instance, in one example, the spinal implant 10 may have a 12 degree lodortic profile from an anterior-posterior (A-P) view.

Figure 3:
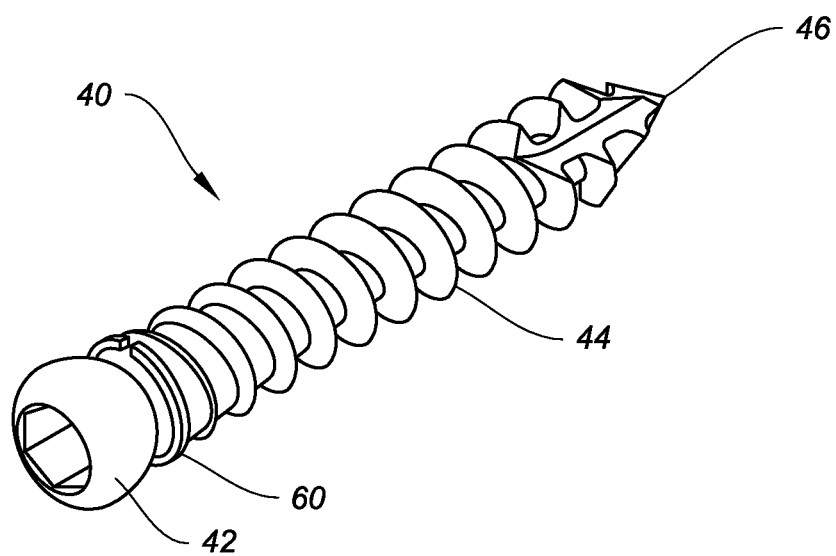
FIG. 3 illustrates an enlarged perspective view of an exemplary fixation screw with locking ring of the present disclosure.
Figure 4:
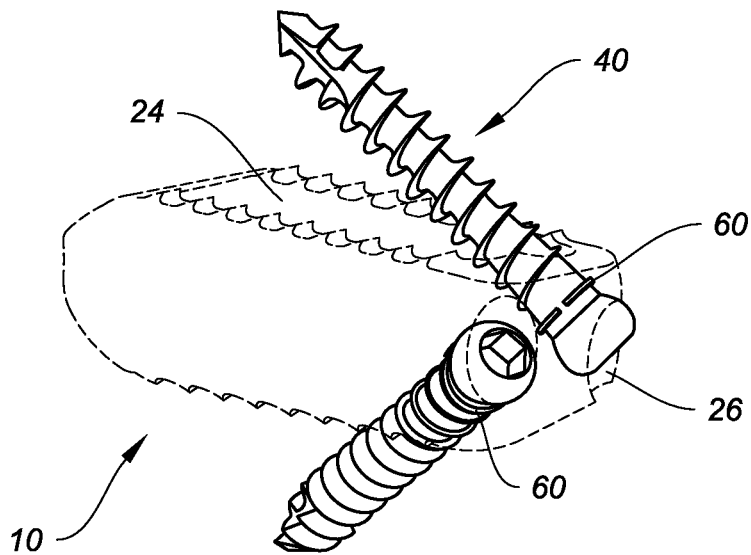
FIG. 4 illustrates a partial cutaway view of the spinal implant of FIG. 1 with the fixation screws and locking rings of FIG. 3.

In some situations, after insertion into the vertebral body, the fixation element or screw 40 may work itself loose and/or back out, i.e., withdraw from the vertebral body. The consequence of back out or loosening includes improper or incomplete fusion, loss of stability, potential risk to the patient, and a separate costly and often painful revision surgery. FIG. 3 shows a fixation screw 40 of the present disclosure, along with an anti-backout element to avoid such problems. As illustrated, the anti-backout element comprises a split ring 60 that acts like a locking ring. FIG. 4 shows the split ring 60 residing between the head 42 of the fixation screw 40 and the hole 26 of the spinal implant 10.

The spinal implant 10 and its components may be formed of any suitable medical grade material, such as biocompatible metals like stainless steel, titanium, titanium alloys, etc. or a medical grade plastic such as polyetheretherketone (PEEK) or another radiolucent material, ultra high molecular weight polyethylene (UHMWPE), etc. If so desired, the implant 10 may also be formed of a bioresorbable material. The bioresorbable material may preferably be osteoconductive or osteoinductive (or both).

In one exemplary method of inserting the spinal implant 10, the surgeon prepares the implantation site by removing some disc material from the disc space 6 between two adjacent vertebrae 2, 4. Because the spinal implant 10 is configured for lateral insertion (i.e., as opposed to midline insertion), less disc material needs to be removed to accommodate the implant 10, which has a slim profile. This provides the benefit of preserving more of the patient's natural anatomy and more specifically, preserves the soft tissue and ligament surrounding the site. The spinal implant 10 may be provided to the surgeon with the screws 40 pre-attached, or separately, as desired. After the surgeon places the implant 10 in the desired location, such as the cervical region of a patient's spine, the surgeon can tighten the screws 40 into the surrounding bone tissue, thereby securing the implant 10.

As noted, the implant 10 may be configured to permit a predetermined amount of screw toggle and enable a lag effect when the fixation screw 40 is inserted and resides inside the hole or lumen 26. Upon tightening, the lag effect may be observed whereby the implant 10 draws bone tissue towards itself, which may promote better fusion.

As further noted, the predetermined screw toggle promotes locking of the screw 40 to the implant 10 after subsidence subsequent to implantation. For example, after surgery, the patient's natural movement will result in settling and subsidence of bone tissue and the implant 10 in situ. It is believed that during this process, the weight exerted upon the implant 10 causes the fixation screws 40 to toggle and eventually lock against one or more surfaces of the holes 26 of the implant 10.

Some practitioners prefer to allow some degree of movement between the implant and the adjacent vertebral body after implantation. In that case the screw heads 42 may be provided with contours on its underside that allow the screws 40 to toggle with respect to the contoured opening 26 of the implant 10. Other practitioners may prefer a more rigid implant that is firmly locked to the adjacent vertebral body. The embodiments of implant 10 allow either preference.

In the rigidly fixed version, the screws 40 may be provided without the contour on its underside (i.e., a relatively flat underside) while the opening 26 of the implant 10 would likewise not include a contour. Thus, when secured together, the screws 40 and implant 10 form a rigidly locked construct. Where rigid fixation is desired (i.e., no toggle), the underside of the screws 40 may also include surfaces features as well in order to provide secure attachment to the implant 10.

While a toggle and a rigidly fixed version of the implant 10 and screws 40 are described, it is understood that a combination of toggling and rigid fixation may be accomplished in a single implant 10. For example, it is possible to provide an implant 10 that allows toggling of one or more screws 40, while also allowing rigid fixation of the other of the screws 40.

It will also be appreciated that the angular positioning of the various holes, as described above, allows the present implant 10 to be of a relatively small size and therefore insertable from a lateral approach within the intervertebral spaces of the spine. Thus, it will be appreciated that the angular positioning of the holes is important to the effective operation of the implant 10 and the ability to "stack" implants in adjacent multilevel procedures without the securing means interfering with each other, which can be of major significance in some situations.

Figure 6A:
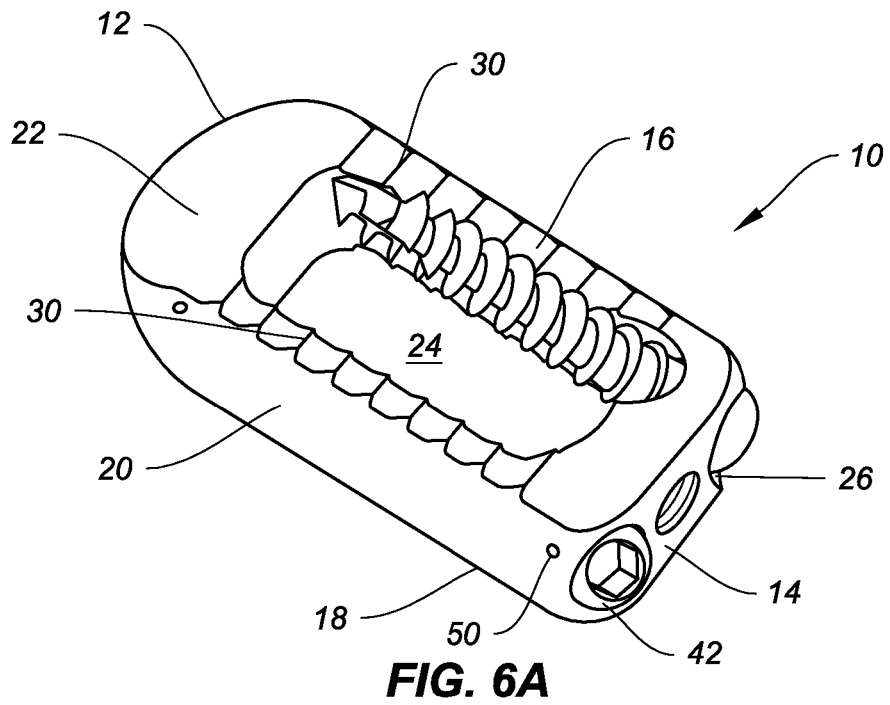
FIG. 6A illustrates a perspective view of an alternative embodiment of a spinal implant of the present disclosure with fixation screws.
Figure 6B:
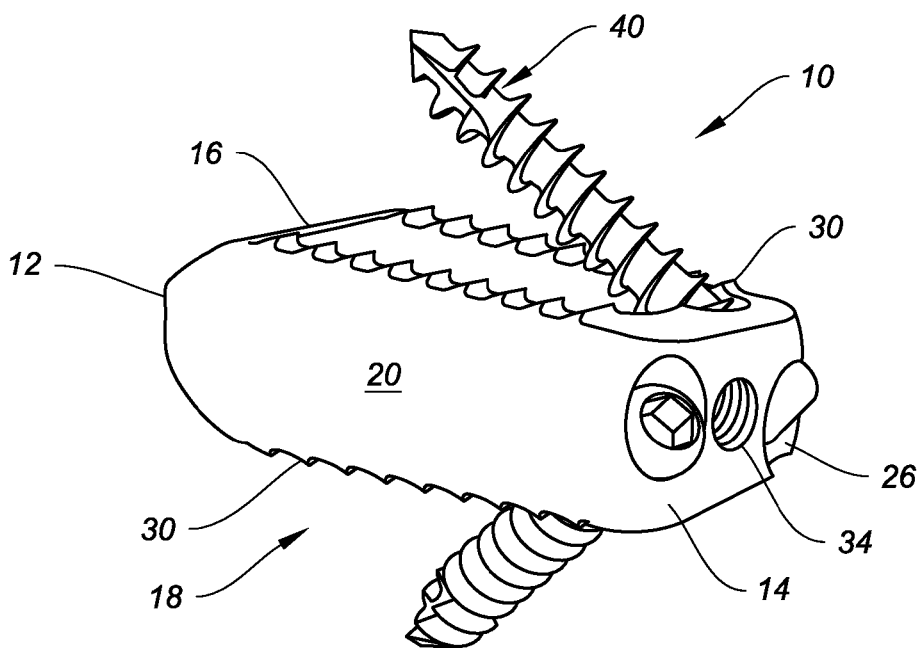
FIG. 6B illustrates another perspective view of the spinal implant and fixation screws of FIG. 6A.

As illustrated, the spinal implant 10 may have any variety of surface features, such as anti-migration and bone attachment features. For example, it is contemplated that the implant may have threads, teeth, barbs, surface roughenings, etc. to assist in bone attachment. Further, biological agents such as bone growth factors, for example, may be employed to enhance bone attachment. FIGS. 6A and 6B illustrate exemplary embodiments of a spinal implant 10 of the present disclosure having teeth 30 on the upper and lower surfaces 16, 18 to prevent migration after implantation and enhance securement to bone tissue.

Other embodiments of the disclosure will be apparent to those skilled in the art from consideration of the specification and practice of the disclosure provided herein. It is intended that the specification and examples be considered as exemplary only.

What is claimed is:

1. A method of treating a patient's spine comprising:
accessing at least a portion of a patient's spine via a lateral approach;
inserting a spinal implant between vertebral bodies of the patient's spine via said lateral approach, wherein the spinal implant comprises a body having an upper surface, a lower surface, an anterior portion, a posterior portion, a pair of substantially planar sidewalls extending in parallel between the upper and lower surfaces, and a central opening extending therethrough between the upper and lower surfaces to facilitate bony ingrowth therethrough, the upper surface and lower surface being non-parallel such that one of the pair of sidewalls has a greater height than the other sidewall to form a wedge-shaped body configured for lateral insertion between vertebral bodies of a patient's spine, the anterior portion comprising a leading edge formed from panels extending from the upper and lower surfaces at an angle relative to one another and converging at a sharpened tip to allow concomitant distraction of soft tissue during insertion, the implant further including one or more apertures within the posterior portion of the body for receiving at least one fixation element; and
attaching the spinal implant with the at least one fixation element to one of the vertebral bodies.

2. The method of claim 1, wherein the spinal implant comprises one or more bores for receiving an imaging marker, and further including the step of inserting the spinal implant based on visual cues provided by the imaging marker.

3. The method of claim 1, wherein inserting the spinal implant comprises inserting the spinal implant based on visual cues provided by a radiopaque imaging marker on an intraoperative image.

4. The method of claim 1, wherein inserting the spinal implant also includes distracting soft tissue with the anterior portion.

5. The method of claim 1, wherein at least one of the apertures is configured to permit a predetermined amount of nutation by the fixation element, and further including the step of permitting a predetermined amount of toggling of the fixation element based on nutation of the fixation element during subsidence of the spinal implant.

6. The method of claim 1, further being repeated for insertion of another similar spinal implant via a lateral approach at a different level of the spine.

* * * * *